(12) United States Patent
Gruslin et al.

(10) Patent No.: US 6,349,471 B1
(45) Date of Patent: Feb. 26, 2002

(54) RAZOR CARTRIDGE WITH PAINTED AND DRAWN RETAINING CLIP

(75) Inventors: Marc R. Gruslin, Mansfield; Paul Flaherty, Pembroke; Robert W. Smith; Matthew J. Guay, both of North Attleboro, all of MA (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 09/619,355

(22) Filed: Jul. 19, 2000

(51) Int. Cl.[7] .............................................. B26B 21/02
(52) U.S. Cl. ......................................................... 30/50
(58) Field of Search ........................... 30/50, 32, 346.5, 30/346.57, 346.54, 350; 76/104.1, DIG. 6, DIG. 8

(56) References Cited

U.S. PATENT DOCUMENTS

| 4,285,528 A | | 8/1981 | Neamtu ....................... 279/2 R |
|---|---|---|---|
| 4,321,846 A | | 3/1982 | Neamtu ....................... 82/36 R |
| 4,932,122 A | * | 6/1990 | Shurland et al. ................ 30/50 |
| 5,010,646 A | | 4/1991 | Neamtu ........................... 30/50 |
| 5,303,539 A | | 4/1994 | Neamtu ........................... 59/75 |
| 5,416,974 A | * | 5/1995 | Wain ............................... 30/50 |
| 5,458,025 A | | 10/1995 | Neamtu ....................... 76/104.1 |
| 5,761,814 A | * | 6/1998 | Anderson et al. ............... 30/50 |
| 5,813,293 A | * | 9/1998 | Apprille et al. ................. 30/50 |
| 6,044,542 A | * | 4/2000 | Apprille et al. ............. 30/50 X |
| 6,161,287 A | * | 12/2000 | Swanson et al. ................ 30/50 |

* cited by examiner

Primary Examiner—Douglas D. Watts
(74) Attorney, Agent, or Firm—Fish & Richardson P.C.

(57) ABSTRACT

A shaving razor cartridge including a housing having an upper surface, a housing opening in the upper surface and side surfaces extending downward from the upper surface, blades mounted in the opening and supported by the housing, and a retaining clip on the upper surface having a clip opening around the housing opening. The retaining clip is made of flat painted sheet metal that has been drawn so as to provide an upper surface extending outward of the clip opening and side surfaces extending downward over the side surfaces of the housing. The paint on the sheet metal has sufficient delamination properties to pass a delamination test involving drawing a piece of flat painted sheet metal such that the paint is compressed greater than 35% and inspecting the resulting drawn piece of sheet metal to see there has been delamination of the paint.

20 Claims, 4 Drawing Sheets

RAZOR CARTRIDGE WITH PAINTED AND DRAWN RETAINING CLIP

BACKGROUND

The invention relates to shaving razors having retaining clips that have been drawn from painted sheet metal and to testing the delamination characteristics of painted sheet metal.

Sheet metal that has been painted can thereafter be formed into a desired shape for a product. The application of paint to the metal is often accomplished via a so-called "roll-coating" process in which a wave of paint is advanced along a sheet of metal passing through a series of rollers. The roll-coating industry has adopted various tests for measuring delamination resistance of painted sheet metal. These tests include a lead pencil test in which leads of different hardness are used to scratch a painted surface and a T-bend test in which a piece of sheet metal is folded back on itself, and adhesive tape is secured to the paint at the bend to see if the tape can pull the paint off at the bend Sheet metal has been used to make clips that retain blades on a shaving razor cartridge. Such retaining clips contact the skin and are highly visible to the user. It is therefore important that, if such clips are made from painted material, the formed clips should be free of delaminated areas for performance, comfort and visual esthetics reasons.

SUMMARY

In one aspect, the invention features, in general, a shaving razor cartridge including a housing having an upper surface, a housing opening in the upper surface and side surfaces extending downward from the upper surface. Blades are mounted in the opening and supported by the housing, and a retaining clip is secured on the upper surface and has a clip opening around the housing opening. The retaining clip is made of flat painted sheet metal that has been drawn so as to provide an upper surface extending outward of the clip opening and side surfaces extending downward over the side surfaces of the housing. The paint on the sheet metal has sufficient delamination properties to pass a delamination test involving drawing a piece of flat painted sheet metal such that the paint is compressed greater than 35% and inspecting the resulting drawn piece of sheet metal to see if there has been delamination of the paint.

In other aspects, the invention features, in general, a retaining clip for a shaving razor as already described and a drawn product made from a piece of sheet metal that has been painted and thereafter drawn, the paint on the sheet metal having sufficient delamination properties to pass a delamination test as already described.

In another aspect, the invention features, in general, a method of determining whether painted sheet metal has sufficient delamination properties for use in a drawn product. The method involves drawing a piece of the flat painted sheet metal such that paint on the sheet metal is compressed to a predetermined percentage, and inspecting the resulting drawn piece of sheet metal to see there has been delamination.

In another aspect, the invention features, in general, a method of making a drawn product, e.g., a retaining clip for a razor cartridge, from painted sheet metal. The method involves drawing a sample piece of the painted sheet metal such that paint on the sheet metal is compressed to a predetermined percentage, inspecting the resulting drawn piece of sheet metal to see there has been delamination, and, if the inspected piece does not have delamination, drawing pieces of the sheet metal into the form for the drawn product.

Particular embodiments of the invention may include one or more of the following features. The paint on a portion of the clip is subjected to compression between 43% and 45.5%. The drawing of the sample piece involves drawing a circular piece of flat painted sheet metal into a cup shape. The inspecting for delamination involves examination of an edge of the drawn sample piece of sheet metal under magnification. The percentage of compression employed when drawing the sample piece can be determined by carrying out drawing of sample pieces of sheet material a series of times at different percentages of compression, and determining which level of compression most accurately predicts delamination in the drawn product.

Embodiments of the invention may include one or more of the following advantages. The testing of stock painted sheet metal material involves more aggressive drawing than the formation of the actual product, such that there is a high confidence that material passing the testing will not delaminate in manufacture of the formed product. The delamination testing can be adapted and fine-tuned for the particular product being drawn.

Other advantages and features of the invention will be apparent from the following description of a particular embodiment thereof and from the claims.

DETAILED DESCRIPTION

Figure 1:
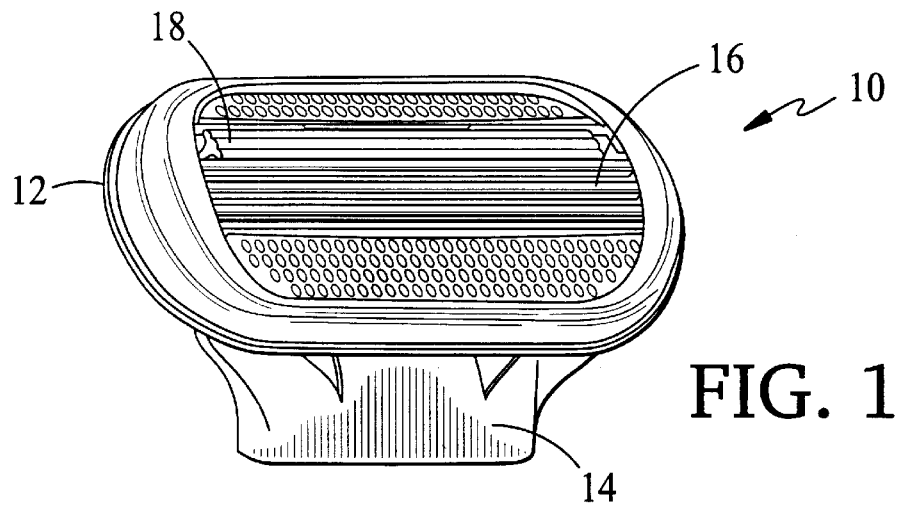
FIG. 1 is a perspective view of a shaving razor cartridge.
Figure 2:
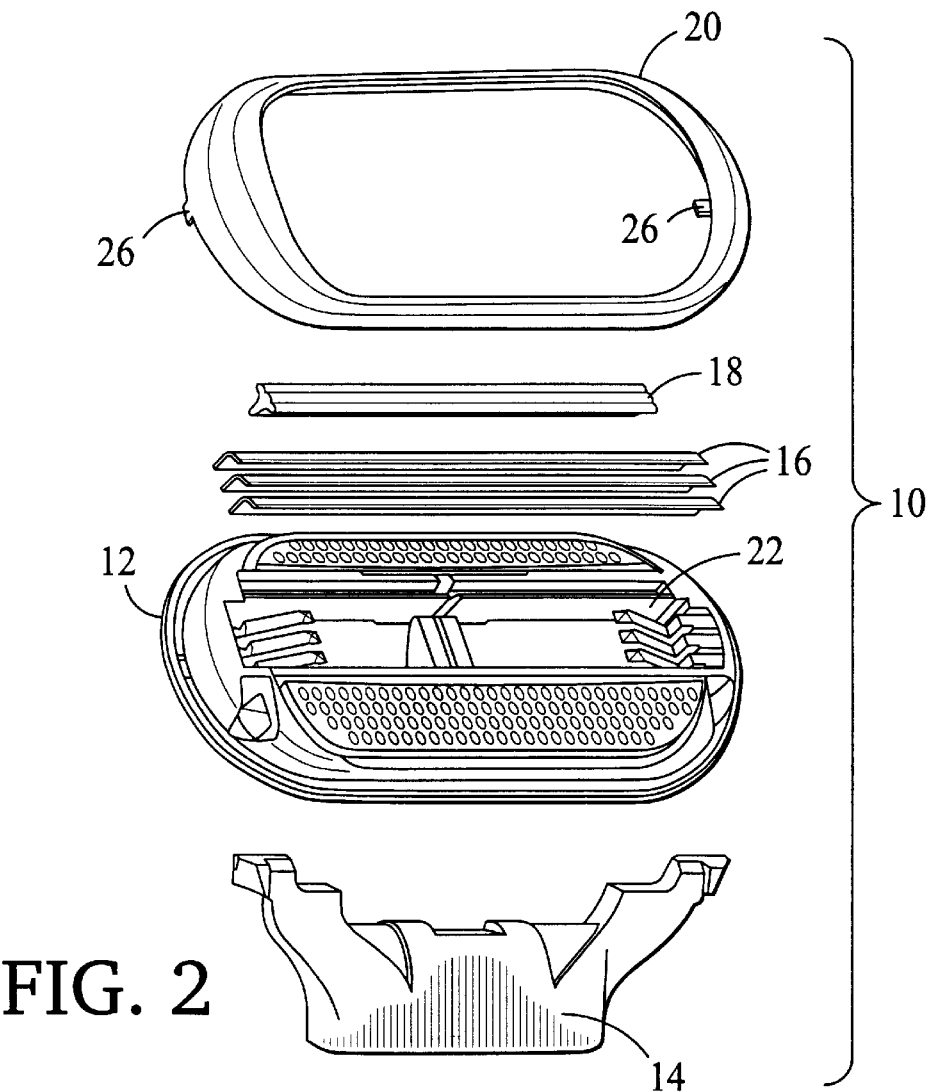
FIG. 2 is an exploded view showing the components of the FIG. 1 shaving razor cartridge.

Referring to FIGS. 1–2, shaving cartridge 10 includes housing 12, pivotal interconnect member 14, blades 16, lubricating strip 18 and retaining clip 20. Blades 16 are mounted in opening 22 in housing 12, and retained therein by clip 20, which fits over the top and sides of housing 12.

Figure 5:
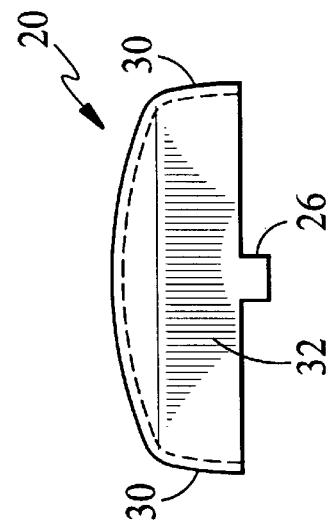
FIG. 5 is a side view of the FIG. 3 retaining clip.
Figure 3:
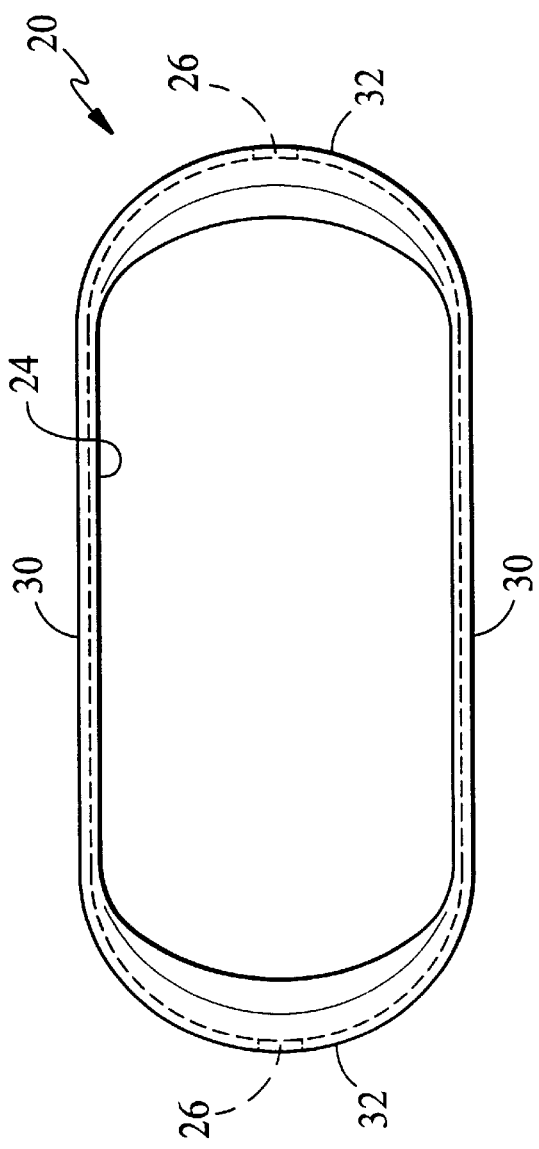
FIG. 3 is a plan view of a retaining clip of the FIG. 1 shaving razor cartridge.
Figure 4:
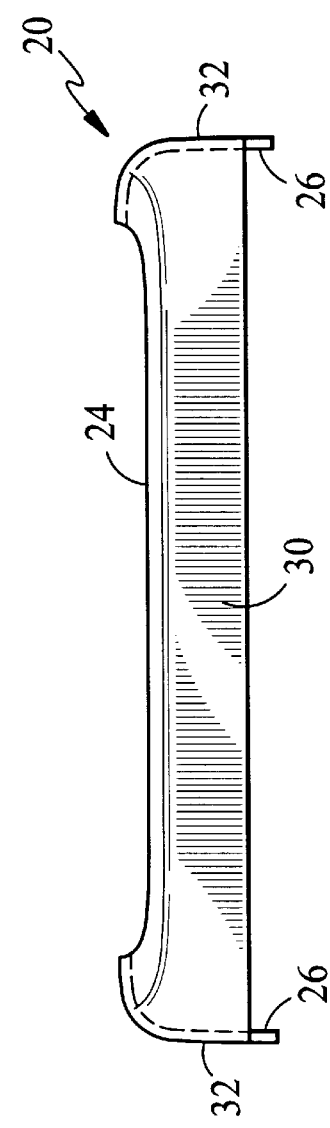
FIG. 4 is an elevation of the FIG. 3 retaining clip.

Referring to FIGS. 3–5, retaining clip 20 has oval shaped opening 24 that surrounds and overlies the sides of opening 22, two retaining tabs 26, upper surface 28 that is curved about an axis parallel to the blades (as seen in FIG. 5), and long and short side surfaces 30, 32, that extend down deeply from the material of upper surface 28. Retaining clip 20 is made from a painted, flat piece of sheet metal that is formed between a die and a punch and then cut to provide opening 24. In the forming process, the material at side surfaces 30, 32 is drawn down deeply from the material of upper surface 28. In such a drawing operation, a portion of sheet material that is larger than the area seen in the top view of FIG. 3 is used and is drawn between the punch and die. In the process, the paint on surfaces 28, 30, 32 (particularly on surfaces 32) is subjected to compression. Compression of the paint can potentially result in delamination, such that the edge surfaces of the paint layer exhibit a rippling that can occasionally be observed with the unaided eye and can in any event be observed under a microscope. In particular, delamination can occur when cutting opening 24 in the formed piece in a stamping operation. If such delamination were present on retaining clips 20 or cartridges 10 containing such clips, the clips and cartridges would not be considered acceptable for use and would need to be discarded.

In the manufacture of retaining clips from painted sheet metal, it was discovered that stock material that passed standard tests used by the roll-coating industry could still be subject to delamination after drawing into the desired shape, and that the extent of delamination varied within materials obtained from different suppliers and even varied within different lots of materials from the same supplier. The term "drawn," as used herein, means that a piece of painted sheet metal has been formed between a punch and die such that the metal is drawn into the die, and the paint on metal being drawn into the die is subject to compression.

Figure 6:
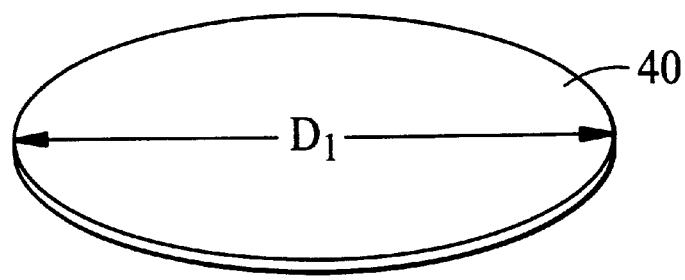
FIG. 6 is a perspective view of a circular sample piece of painted sheet metal to be tested for delamination resistance.
Figure 7:
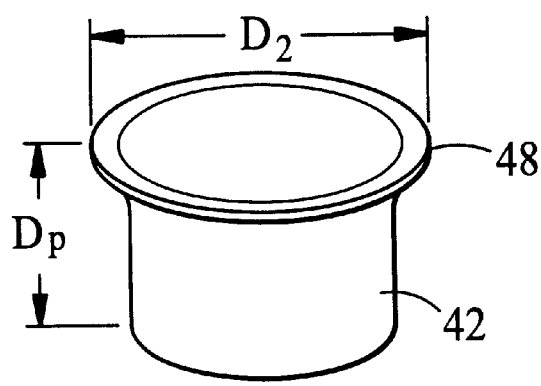
FIG. 7 is a perspective view of a test cup drawn from the FIG. 6 piece of metal.
Figure 8:
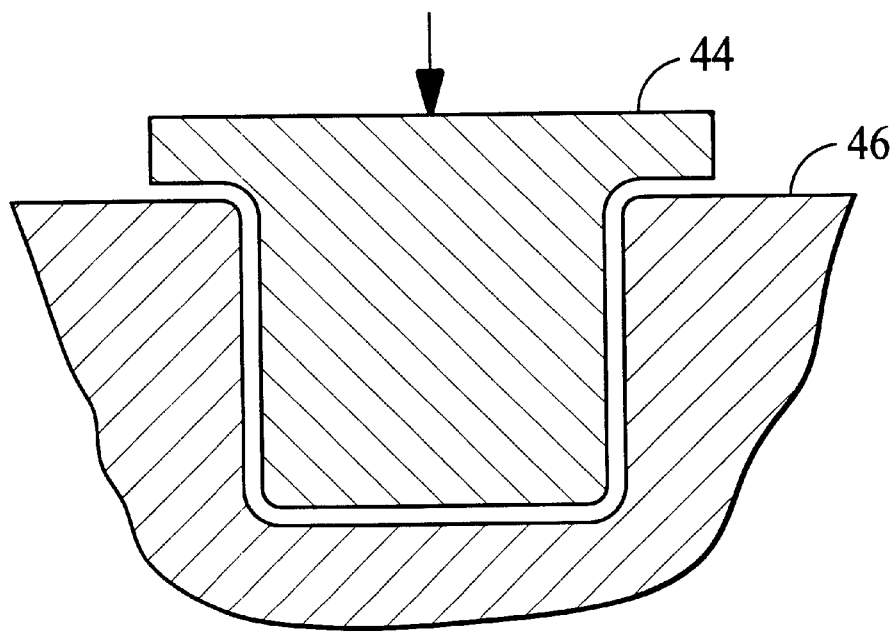
FIG. 8 is a vertical sectional view showing the punch and die used to draw the FIG. 6 piece of metal to result in the FIG. 7 cup.

Referring to FIGS. 6–8, in order to determine whether painted sheet metal stock material has sufficient delamination resistance to avoid delamination after being formed with deep drawing into a retaining clip 20, circular samples 40 are drawn into cups 42 using punch 44 and die 46. Sheet metal piece 40 is 0.018" thick, and the clearance between punch 44 and die 46 is 0.020", thus providing 0.001" average clearance on each side between the material 40 and punch and die 44, 46. Circular sample 40 has a diameter $D_1$ (55mm), and cup 42 has diameter $D_2$. The paint at the perimeter, which reduces in diameter from $D_1$ to $D_2$, has compression of $1-D_2/D_1 \times 100\%$. Thus if a 55mm diameter piece 40 is drawn to form a cup 42 having a diameter of 38 mm, the paint has been subjected to extent of compression of 30.9%. Diameter $D_1$ and the depth of drawing $D_p$ are selected to result in a lip having a radial dimension of at least 1 mm at edge 48.

Figure 9:
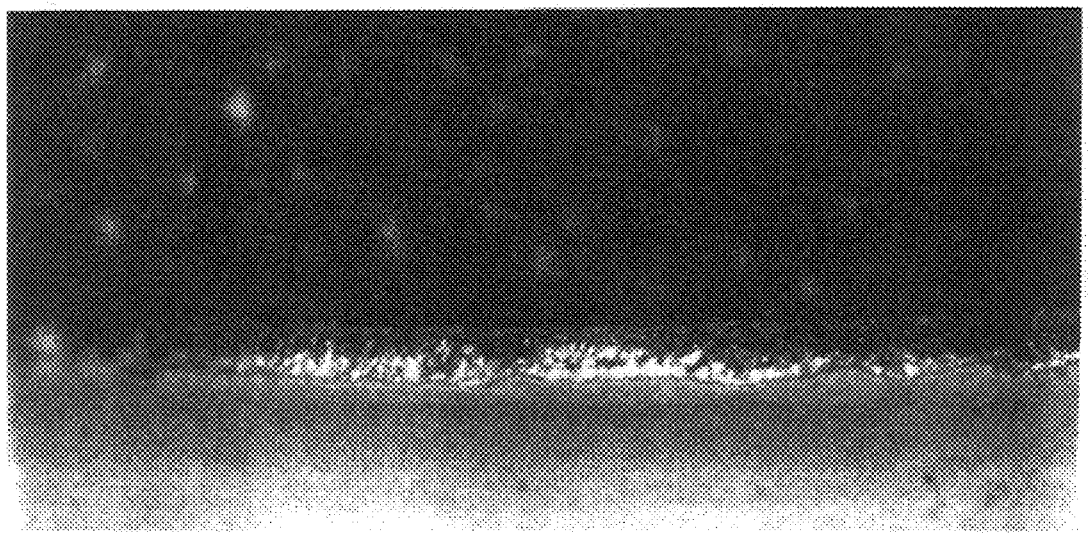
FIGS. 9 and 10 are magnified photographs showing the edges of painted sheet metal after a drawing operation.
Figure 10:
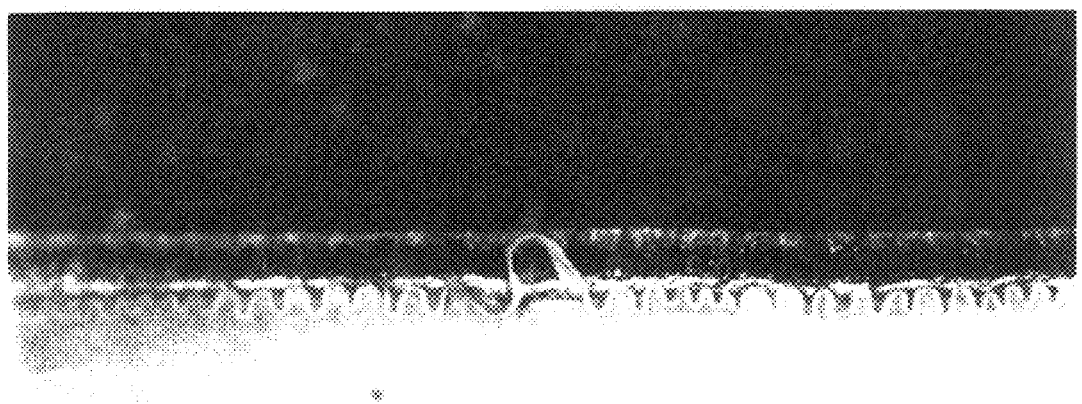

After forming cups 42, the edges 48 are examined using a microscope, e.g., a Nikon SMZ645 at a magnification of 20X. A small amount of disruption of the paint exists on all samples owing to the stamping operation in which the circular samples are cut from the stock material. Where actual delamination occurs, large spaces can be seen between the paint layer and the metal layer. FIG. 9 shows an example of a good painted edge under magnification, and FIG. 10 shows an example of a delaminated edge under magnification.

By varying the diameter $D_2$ and the depth $D_p$ of cup 42, one can precisely vary the extent of compression and thereby precisely assess the extent of delamination resistance of stock sheet material to be subjected to various drawing operations. For example, D2 was varied from 28 mm to 38 mm for circular pieces 40 having a 55 mm diameter that were taken from a variety of lots of material. It was found that the samples drawn to the 28 mm diameter (49.1% compression) always had delamination, that samples drawn to the 30 and 32 mm diameters (45.5% and 41.8% compression, respectively) occasionally had delamination, that samples drawn to the 34 and 36 mm diameters (38.2% and 34.6% compression, respectively) rarely had delamination, and that samples that were drawn to the 38 mm diameter (30.9% compression) never had delamination. The same sheet materials were used to form retaining clips 20, and some were subject to delamination and some were not. It was found that any samples that passed the 30 mm test, with a depth of drawing ($D_p$) of 78 mm, never had any delamination problems in forming retaining rings 20. Thus the 28 mm diameter would not be an effective test, as it would cause all samples to fail, and the 38 mm would not be an effective test as none of the materials would fail even though delamination could result in the actual product. The 30 mm diameter subjects the materials to more aggressive compression than in the manufacture of rings 20, but it does not reject too many materials that might still be drawn without delamination and serves as an effective test.

Other embodiments of the invention are within the scope of the appended claims. For example, the component made by drawing painted sheet metal could be something other than a clip used on a razor cartridge.

What is claimed is:

1. A shaving razor cartridge comprising
    a housing having an upper surface, a housing opening in said upper surface and side surfaces extending downward from said upper surface,
    blades mounted in said opening and supported by said housing, and
    a retaining clip on said upper surface having a clip opening around said housing opening, said retaining clip being made of flat painted sheet metal that has been drawn so as to provide an upper surface extending outward of said clip opening and side surfaces extending downward over said side surfaces of said housing,
    said paint on said sheet metal having sufficient delamination properties to pass a delamination test comprising drawing a piece of said flat painted sheet metal such that said paint is compressed greater than 35% and inspecting the resulting drawn piece of sheet metal to see there has been delamination of said paint.

2. The cartridge of claim 1 wherein paint on a portion of said clip is subjected to compression between 43% and 45.5%.

3. A retaining clip for a shaving razor,
    said clip having a clip opening for exposing the cutting edges of razor blades to be retained thereunder,
    said clip being made from a piece of flat painted sheet metal that has been drawn so as to provide an upper surface extending outward of said clip opening and side surfaces extending downward from said upper surface,
    said paint on said sheet metal having sufficient delamination properties to pass a delamination test comprising drawing a piece of said flat painted sheet metal such that said paint is compressed greater than 35% and inspecting the resulting drawn piece of sheet metal to see there has been delamination.

4. The retaining clip of claim 3 wherein paint on a portion of said clip is subjected to compression between 43% and 45.5%.

5. A drawn product made from a piece of sheet metal that has been painted and thereafter drawn, said paint on said sheet metal having sufficient delamination properties to pass a delamination test comprising drawing a piece of said flat painted sheet metal such that said paint is compressed greater than 35% and inspecting the resulting drawn piece of sheet metal to see there has been delamination.

6. The product of claim 5 wherein paint on a portion of said clip is subjected to compression between 43% and 45.5%.

7. A method of determining whether painted sheet metal has sufficient delamination properties for use in a drawn product comprising
    drawing a piece of said flat painted sheet metal such that paint on said sheet metal is compressed to a predetermined percentage, and inspecting the resulting drawn piece of sheet metal to see there has been delamination.

8. The method of claim 7 wherein said drawing involves drawing so as to result in greater than 35% compression of paint.

9. The method of claim 7 wherein said drawing involves drawing a circular said piece of flat painted sheet metal into a cup shape.

10. The method of claim 9 wherein said inspecting includes examination of an edge of said drawn piece of sheet metal under magnification.

11. The method of claim 7 further comprising prior to said drawing, determining said predetermined percentage by carrying out drawing of said sheet material a series of times at different percentages of compression, and determining which level of compression most accurately predicts delamination in said drawn product.

12. A method of making drawn product from painted sheet metal comprising drawing a sample piece of said flat painted sheet metal from a lot of stock painted sheet metal such that paint on said sheet metal is compressed to a predetermined percentage, inspecting the resulting drawn piece of sheet metal to see there has been delamination, and if said inspected piece does not have delamination, drawing pieces of said lot of sheet metal into the form for said drawn product.

13. The method of claim 12 wherein said drawing said sample piece involves drawing so as to result in greater than 35% compression of paint.

14. The method of claim 13 wherein said drawing pieces of said lot involves drawing so as to result in greater than 35% compression of paint.

15. The method of claim 12 wherein said drawing said sample piece involves drawing a circular said piece of flat painted sheet metal into a cup shape.

16. The method of claim 15 wherein said inspecting includes visually inspecting an edge of said drawn material under magnification.

17. A method of making a retaining clip for a razor cartridge drawn from painted sheet metal comprising drawing a sample piece of said flat painted sheet metal from a lot of stock painted sheet metal such that paint on said sheet metal is compressed to a predetermined percentage greater than 35%, inspecting the resulting drawn piece of sheet metal to see there has been delamination, and if said inspected piece does not have delamination, drawing pieces of said lot of sheet metal into the form of an oval clip having an upper surface and side surfaces extending downward from said upper surface, and cutting a clip opening in said upper surface for exposing the cutting edges of razor blades to be retained thereunder.

18. The method of claim 17 wherein said drawing pieces of said lot involves drawing so as to result in greater than 35% compression of paint.

19. The method of claim 17 wherein said drawing said sample piece involves drawing a circular said piece of flat painted sheet metal into a cup shape.

20. The method of claim 17 wherein said inspecting includes visually inspecting an edge of said drawn material under magnification.

* * * * *